US008857437B2

(12) United States Patent
Powell, III

(10) Patent No.: US 8,857,437 B2
(45) Date of Patent: Oct. 14, 2014

(54) PROPHYLACTIC DEVICE AND METHODS OF USE

(71) Applicant: Charles A. Powell, III, Torrance, CA (US)

(72) Inventor: Charles A. Powell, III, Torrance, CA (US)

(73) Assignee: Charles A. Powell, III, Torrance, CA (US)

(*) Notice: Subject to any disclaimer, the term of this patent is extended or adjusted under 35 U.S.C. 154(b) by 54 days.

(21) Appl. No.: 13/647,372

(22) Filed: Oct. 8, 2012

(65) Prior Publication Data

US 2014/0096776 A1  Apr. 10, 2014

(51) Int. Cl.
A61F 6/04 (2006.01)
(52) U.S. Cl.
USPC ........................................... 128/844; 128/918
(58) Field of Classification Search
CPC ............. A61F 6/02; A61F 6/04; A61F 5/451; A61F 5/453
USPC ........... 128/842, 844, 918; 604/347, 349, 351
See application file for complete search history.

(56) References Cited

U.S. PATENT DOCUMENTS

| 4,320,752 A | 3/1982 | Comparetto |
| 4,769,020 A | 9/1988 | Eaton |
| 4,821,742 A | 4/1989 | Phelps, III |
| 5,458,114 A * | 10/1995 | Herr ............................ 128/842 |
| 6,148,819 A | 11/2000 | Winkler |
| 6,491,035 B2 | 12/2002 | Winkler |
| 6,699,226 B2 * | 3/2004 | Velazquez .................... 604/349 |
| 2011/0230851 A1 | 9/2011 | Kay |
| 2014/0076329 A1 * | 3/2014 | Rhodes ......................... 128/844 |

* cited by examiner

Primary Examiner — Patricia Bianco
Assistant Examiner — Camtu Nguyen
(74) Attorney, Agent, or Firm — Robert D. Becker; Manatt, Phelps & Phillips LLP

(57) ABSTRACT

A prophylactic device having a base substrate for adhering to a glans of a penis, and a reservoir cap having a reservoir and a flange for adhering to the base substrate. The base substrate may be a thin polyurethane film coated with a pressure-sensitive adhesive for adhering to the skin of the glans. The flange of the reservoir cap has a pressure-sensitive adhesive for adhering to the base substrate. A security ring is also provided for adhering to and covering the junction of the bottom edge of the flange and base.

14 Claims, 15 Drawing Sheets

PROPHYLACTIC DEVICE AND METHODS OF USE

FIELD OF THE INVENTION

The present invention generally relates to medical devices. More particularly, preferred embodiments of the invention relate to male sexual barrier devices or prophylactics and methods for using the same.

BACKGROUND OF THE INVENTION

Condoms and other male sexual barrier devices cover a penile glans, and utilize a roll-down tube to cover a penile corpus and to provide contact area for fixation to the penis by maintaining as much friction resistance as need between the barrier material and the penis to avoid accidental repositioning, removal, or leakage of the device during coitus. A disadvantage of such barrier devices is their reduced use during sexual activity due to reduced pleasure caused by the covering of sensitive penile areas.

Approaches for overcoming such disadvantages include barriers of a reduced size, thereby exposing regions such as the penile corpus for pleasurable contact during coitus. Such barriers are installed on a penile glans by distributing pressure-sensitive adhesive to the underside of the barrier for installation of the barrier directly onto the glans skin. Disadvantages to such approaches include an imperfect seal of the device. In another approach, liquid adhesive is applied to the glans skin for adhering the barrier to the glans. Disadvantages of this approach includes the lack of precise application, messiness, spillage risk, and other inconveniences of using a liquid adhesive.

BRIEF SUMMARY OF PREFERRED EMBODIMENTS OF THE INVENTION

A preferred embodiment of the invention includes a multi-part device having a reservoir cap, the reservoir cap having a reservoir, and a flange around the opening of the reservoir. The multi-part device further includes a base onto which the reservoir cap may be adhered or bonded, the base for adhering to a penile glans. The multi-part device includes a security ring for securing the reservoir cap to the base. A method of using the device is described the method including applying a multi-part base to a glans, applying the reservoir cap to the base, and applying a security ring to the flange and the base, the security ring having an opening through which the reservoir is inserted and covering at least the flange and the base for further avoiding leaks from the reservoir at the base-reservoir-cap junction.

BRIEF DESCRIPTION OF THE DRAWINGS

Preferred embodiments of the present invention are illustrated by way of example, and not by way of limitation, in the figures of the accompanying drawings and in which like reference numerals refer to similar elements and in which.

DETAILED DESCRIPTION OF PREFERRED EMBODIMENTS OF THE INVENTION

Figure 1:
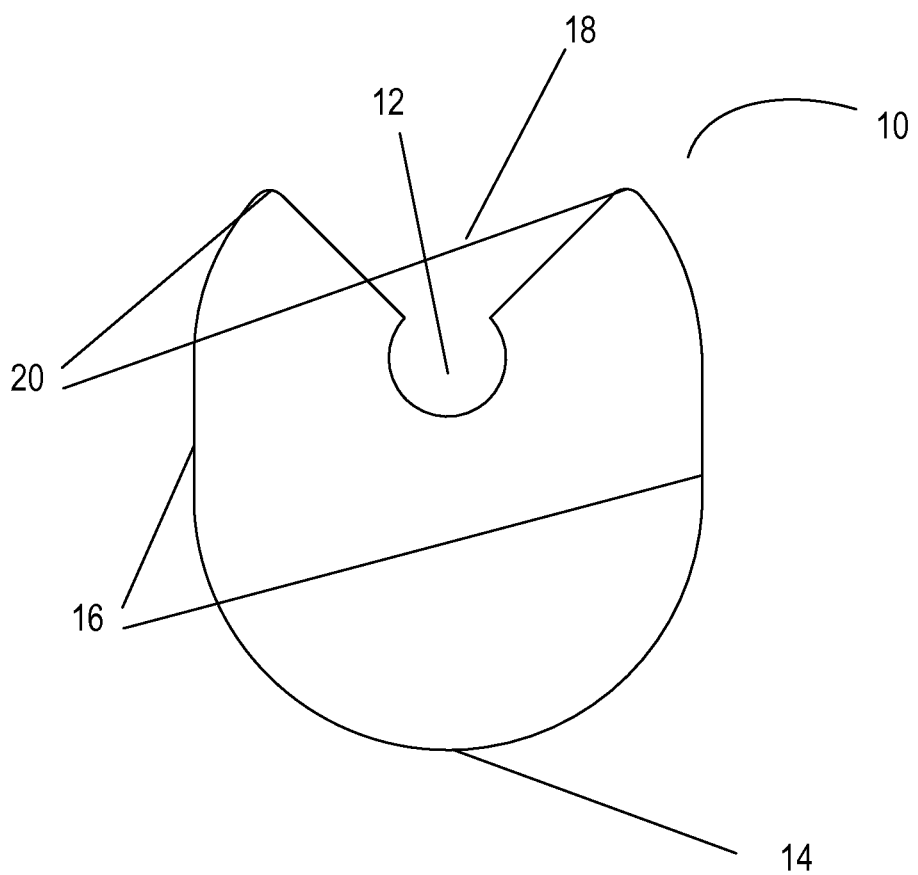
FIG. 1 is a diagrammatic view of a first base portion of the prophylactic device for applying to a penile glans centered on a dorsal side of the glans, according to some embodiments of the invention.

FIG. 1 illustrates an example of a first base portion 10 of the prophylactic device according to embodiments of the invention. First base portion 10 comprises a patch of a material coated with adhesive that provides a liquid barrier for the covered area, such as the translucent or transparent medical-grade adhesive film, for example model number 9832, 9833 or 9834, manufactured by the 3M Company. According to embodiments of the invention, materials used for first base portion 10 include polyurethane and other flexible materials. In some embodiments, first base portion 10 has a removable carrier backing layer adhered to the top side of the film for ease of application of the film. In some embodiments, first base portion 10 has a removable protective backing on the adhesive coating to protect the coating from undesired adhesion before application. While in this example, first base portion 10 is a single-coated material with adhesive on one side of the film, in other examples, a double-sided adhesive film or tape can be used without departing from the spirit of embodiments of the invention. Adhesive coatings used for first base portion 10 and for applying to other portions of the prophylactic device include pressure-sensitive adhesive coatings or other adhesives suitable for adhering a flexible material onto skin. Tape model number 9832, 9833, or 9834, by the 3M Company, are examples of flexible materials coating with pressure-sensitive adhesive coating. While the examples herein are described as using pressure-sensitive adhesive coatings, any adhesives suitable for adhering a flexible material onto skin are contemplated within the scope of embodiments of the invention.

First base portion 10 provides an opening 12 to avoid obstructing the meatus of the penis when in use. First base portion 10 is shaped to allow coverage of portions of at least the dorsal side of a glans when applied. In the example as shown, first base portion 10 includes a round bottom edge 14, straight sides 16, and a wedge-shaped opening 18 that appears as being cut out from a round top edge, although the shape may be formed by other techniques. In some embodiments, the shape is cut from a flat material, including by die cutting techniques. In some embodiments, the shape is formed from a material by molding, extruding, or other methods of producing material that can be used for first base portion 10. In other embodiments, first based portion 10 is formed from an oblong patch with opening 12, having a slit from opening 12 to the top edge.

In further reference to FIG. 1, points 20 are rounded to avoid sharp contact with sensitive skin areas. While the example as shown has a particular shape, it is understood that other embodiments may vary in shape without departing from the spirit of the invention.

Figure 2:
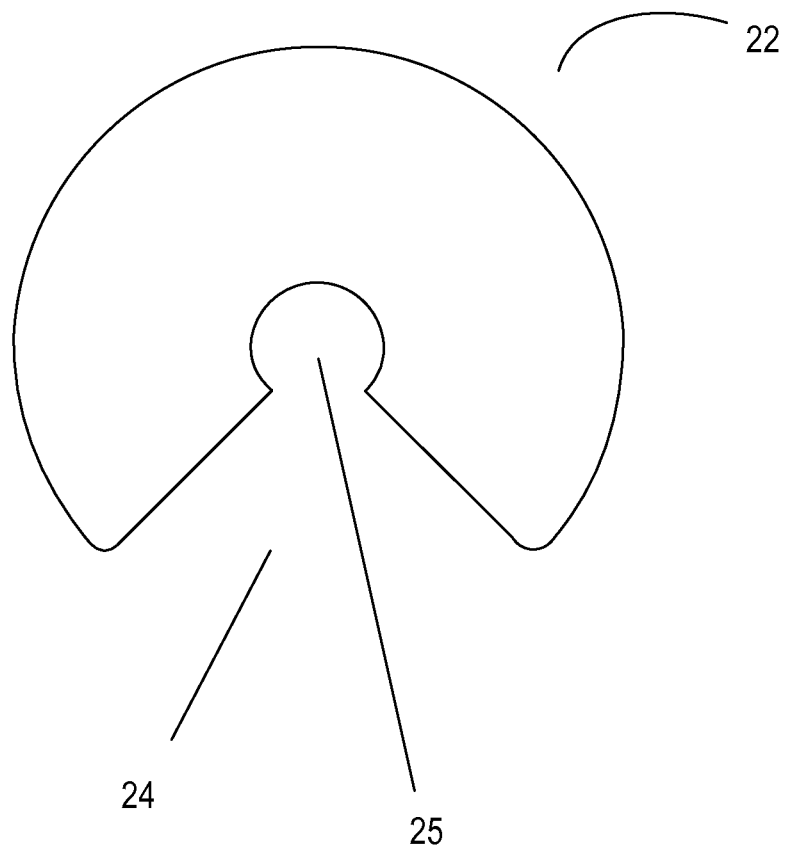
FIG. 2 is a diagrammatic view of a second base portion of the prophylactic device for applying to a penile glans centered on a ventral side of the glans, according to some embodiments of the invention.

FIG. 2 illustrates an example of a second base portion 22 of the prophylactic device according to embodiments of the invention. Second base portion 22 comprises a patch of material coated with pressure-sensitive adhesive, such as the example described above with reference to FIG. 1. In some embodiments, second base portion 22 has a removable carrier backing layer adhered to the top side of the film for ease of application of the film. In some embodiments, second base portion 22 has a removable protective backing on the adhesive coating to protect the coating from undesired adhesion before application. Second base portion 22 appears as a ring with a wedge-shaped opening 24 cut of therefrom. The shape allows second base portion 22 to provide coverage to the surface contour of the ventral side of the penis when applied thereto, when approximately centered on the ventral midline. Second base portion 22 has an opening 25 to avoid obstructing the meatus of the penis when in use. While the example as shown has a particular shape, it is understood that other embodiments may vary in shape without departing from the spirit of the invention. In some embodiments, first base portion 10 is a shape that covers a sufficient area of the penile glans. In such embodiments, second base portion 22 is not necessary.

Figure 3:
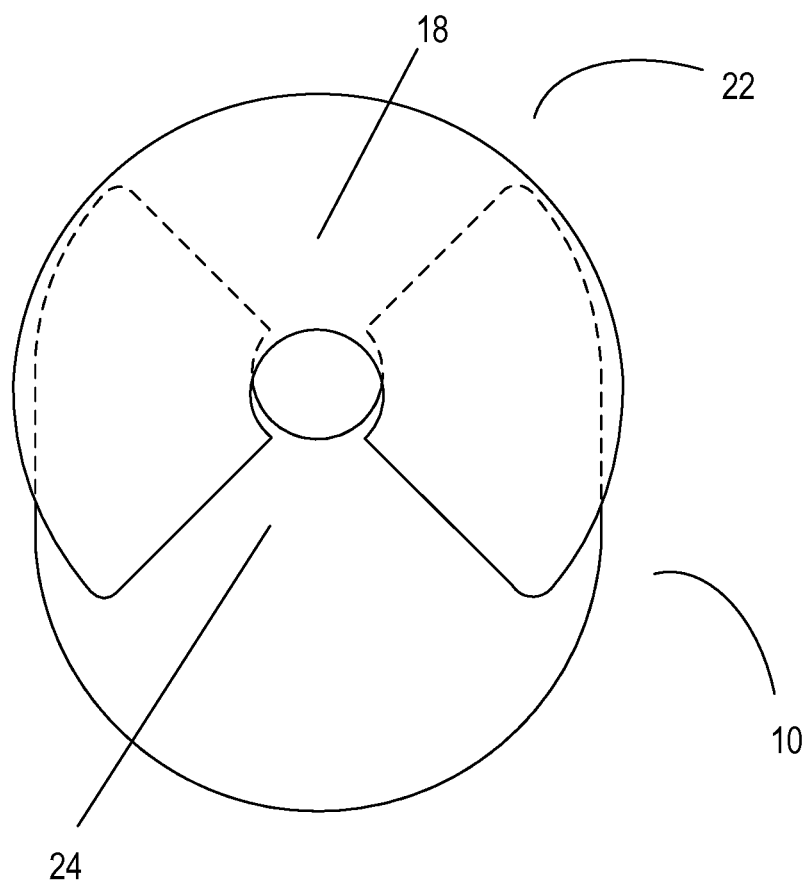
FIG. 3 is diagrammatic view of the relative approximate positions of a first base and a second base portion of the prophylactic device when in use to form a base, according to some embodiments of the invention.

FIG. 3 illustrates an example of the first base portion 10 and second base portion 22, and their rough relative opposing positions when arranged and applied to cover a penile glans according to some embodiments of the invention. According to some embodiments, when in use, wedge openings 18 and 24 come closer together, or may overlap, as the base portions 10 and 22 are adhered to the surface contour of the penile glans.

Figure 4:
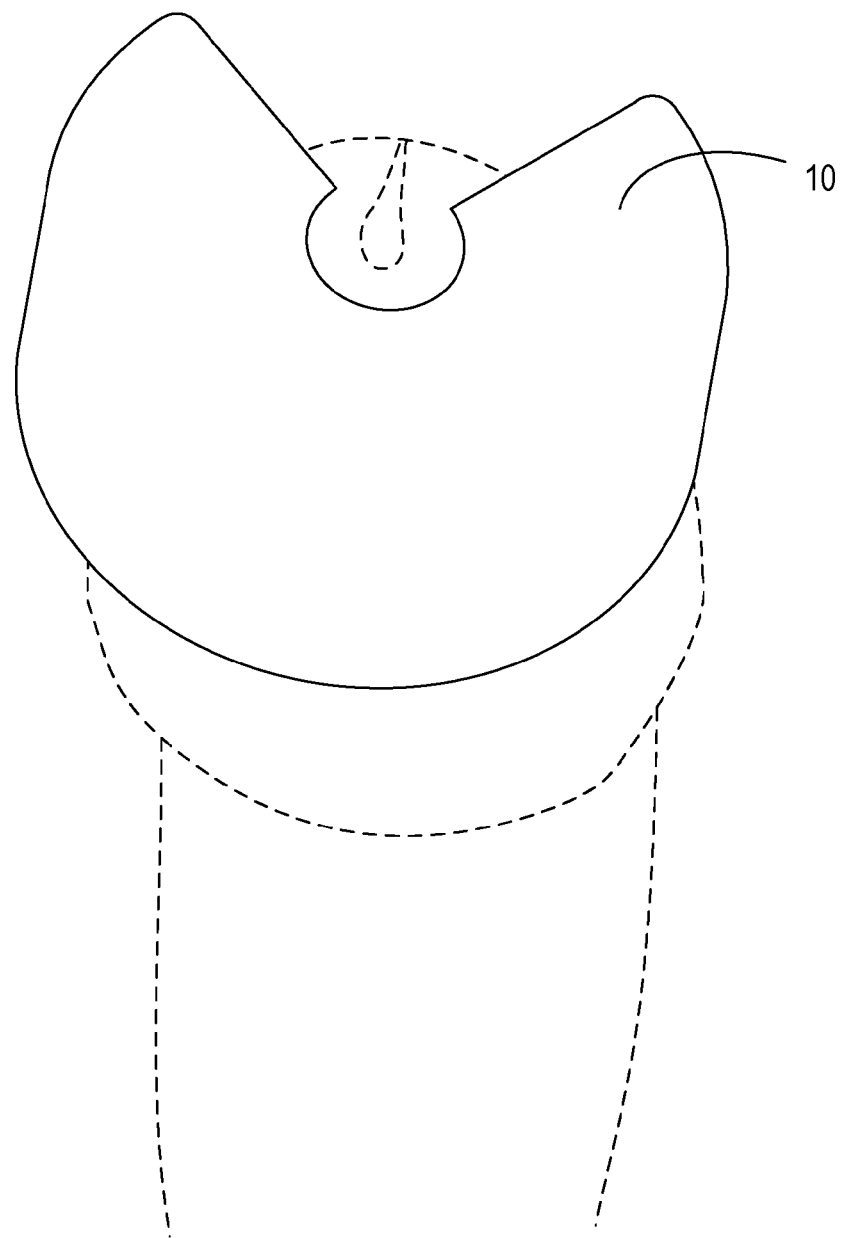
FIG. 4 is a diagrammatic view of the first portion of the prophylactic device as applied to a dorsal side of a penile glans, according to some embodiments of the invention.

FIG. 4 illustrates an example of first base portion 10 as it is applied to the dorsal side of the penile glans. In some embodiments, one pressure-sensitive adhesive side of first base portion 10 is exposed for adhesion to the penis. First base portion 10 is adhered to the dorsal side of the glans centered approximately along the dorsal midline.

Figure 5:
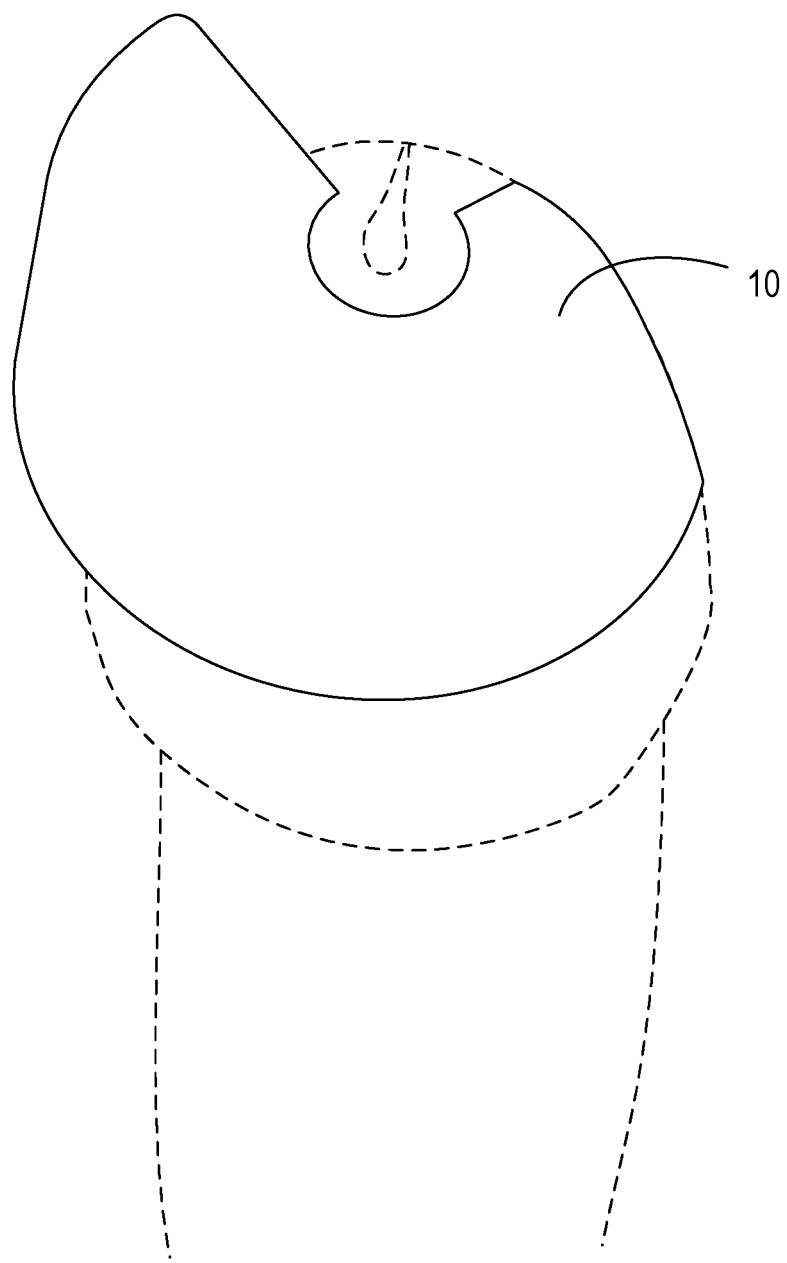
FIG. 5 is a diagrammatic view of the first portion of the prophylactic device as shown being applied to the penile glans, according to some embodiments of the invention.

FIG. 5 illustrates a example view of first base portion 10 as it is applied to the dorsal side of the penile glans. As shown, the right-hand portion is wrapped around and adhered to the surface contour of the penile glans.

Figure 6:
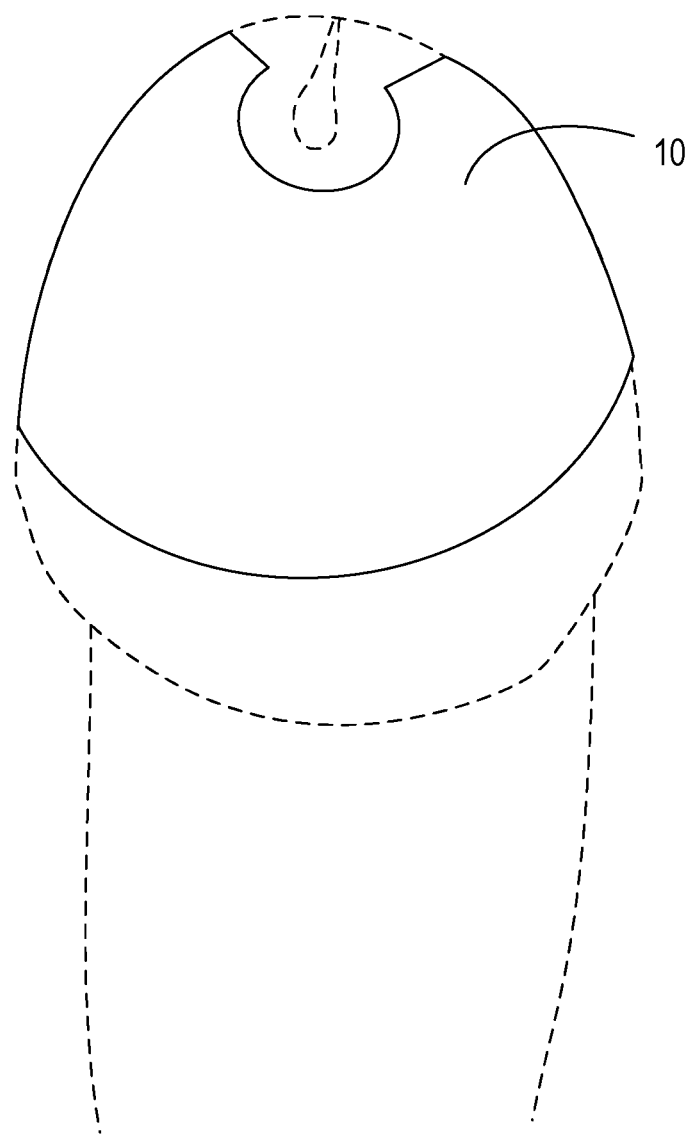
FIG. 6 is a diagrammatic view of the first portion of the prophylactic device as shown with application completed on the penile glans, according to some embodiments of the invention.

FIG. 6 illustrates an example view of first base portion 10 upon being fully applied to the dorsal side of the penile glans. As shown, the exposed adhesive side of first base portion 10 is adhered to the penile glans, forming around the surface contour.

Figure 7:
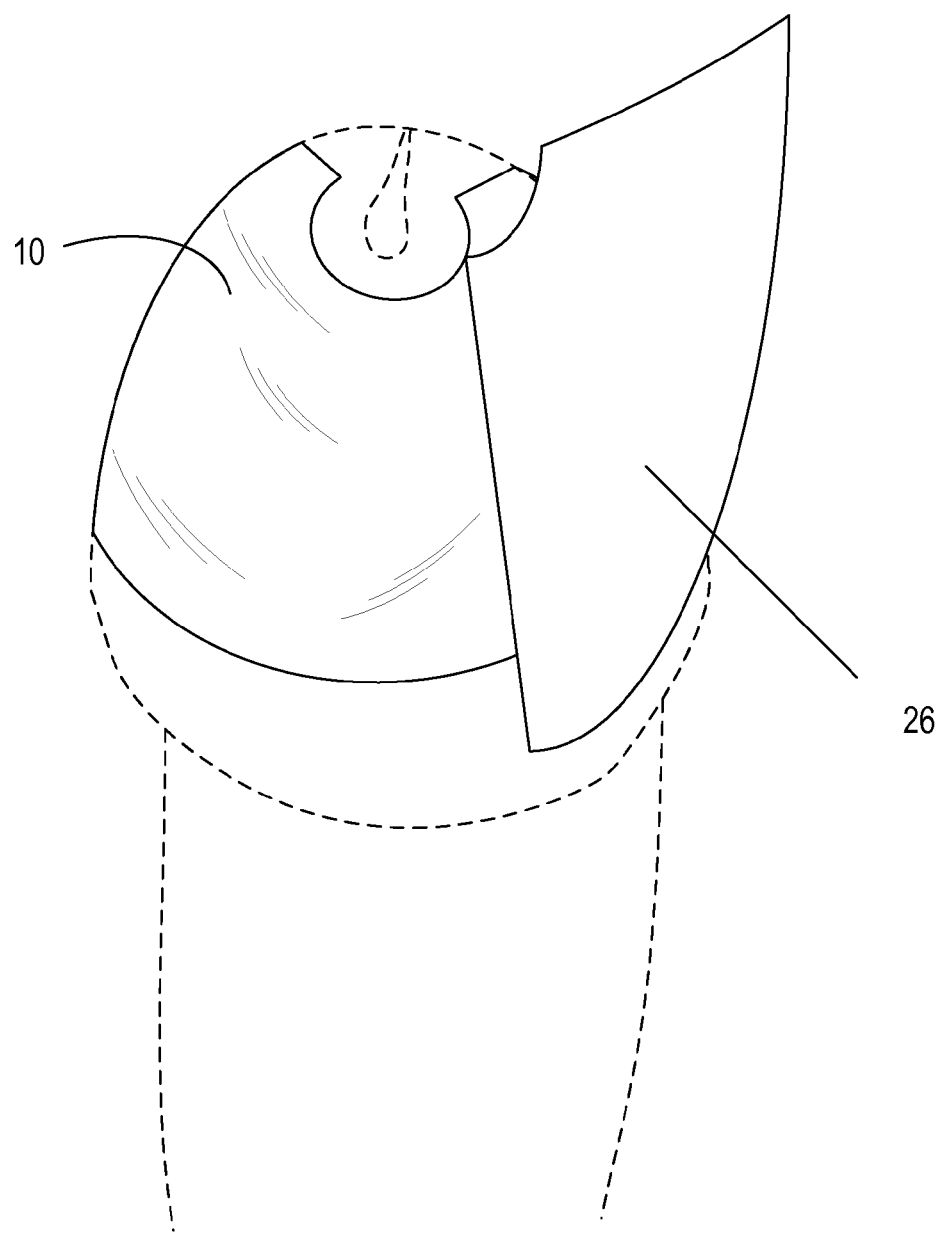
FIG. 7 is a diagrammatic view of the first portion of the prophylactic device as shown with application completed on the penile glans and with carrier layer being removed, according to some embodiments of the invention.

FIG. 7 illustrates an example view of layer 26 of carrier backing removed from first base portion 10 after the first base portion 10 is adhered to the glans. In this example, layer 26 is a carrier backing for preventing the material of first base portion 10 from collapsing on itself during handling. While the embodiments described above include the use of a carrier backing on the adhesive film, it is understood that other adhesive films may use no carrier backing, and do not depart from the spirit of embodiments of the invention. When the backing is removed, the exposed surface of first base portion 10 is not adhesive in this example, although the exposed surface may be coated with adhesive without departing from the spirit of the invention.

Figure 8:
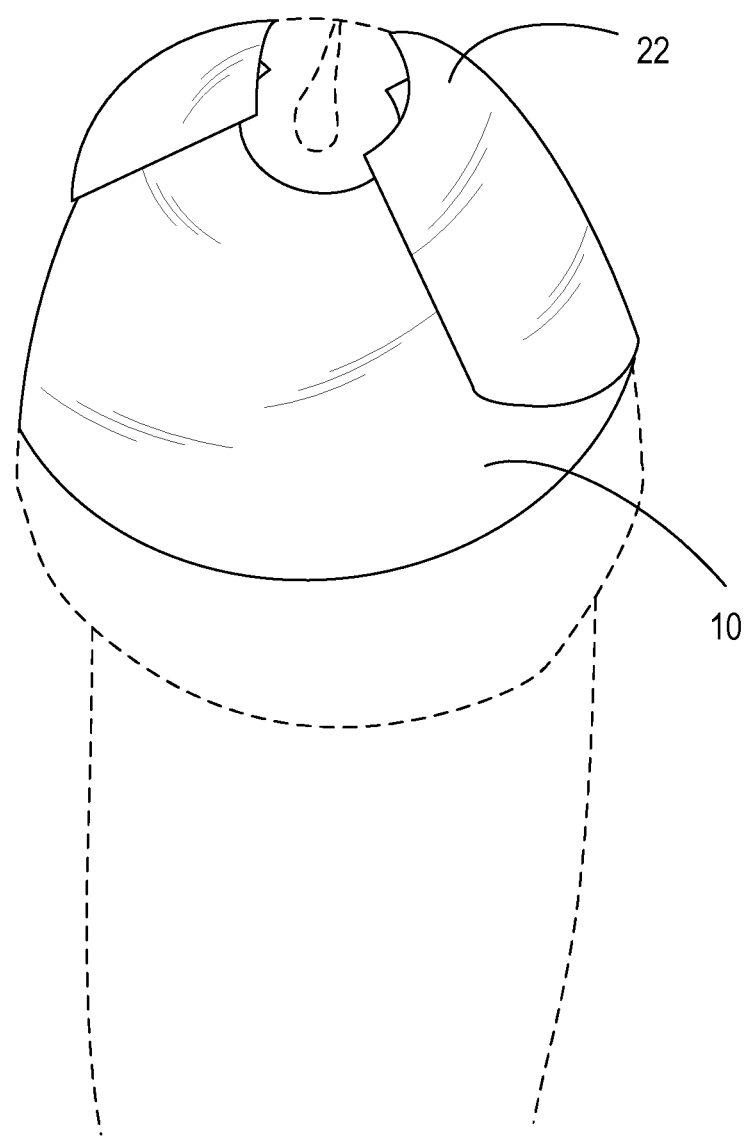
FIG. 8 is a diagrammatic view of the first and second portions of the prophylactic device as shown with application completed on both the dorsal and ventral sides of the penile glans, and with both carrier layers removed, according to some embodiments of the invention.

FIG. 8 illustrates an example view of both first base portion 10 and second base portion 22 after application to the penile glans. The ends of second base portion 22 are shown wrapping around to the dorsal side from the ventral side of the glans. The second base portion 22 was applied in a fashion similar to the way first base portion 10 is applied as shown in FIGS. 4-7. As shown, first base portion 10 and second base portion 22 as applied leave an opening over the meatus to allow unobstructed output of bodily fluids. This configuration allows for extended-wear of the base portions to reduce the steps of application during sexual activity. First base portion 10 and second base portion 22 forms a completed base substrate onto which other objects may be adhered. The base substrate provides a seal between it and the glans skin such that ejaculate, or components therein, do not pass underneath the seal from one edge of the base to another.

Figure 9:
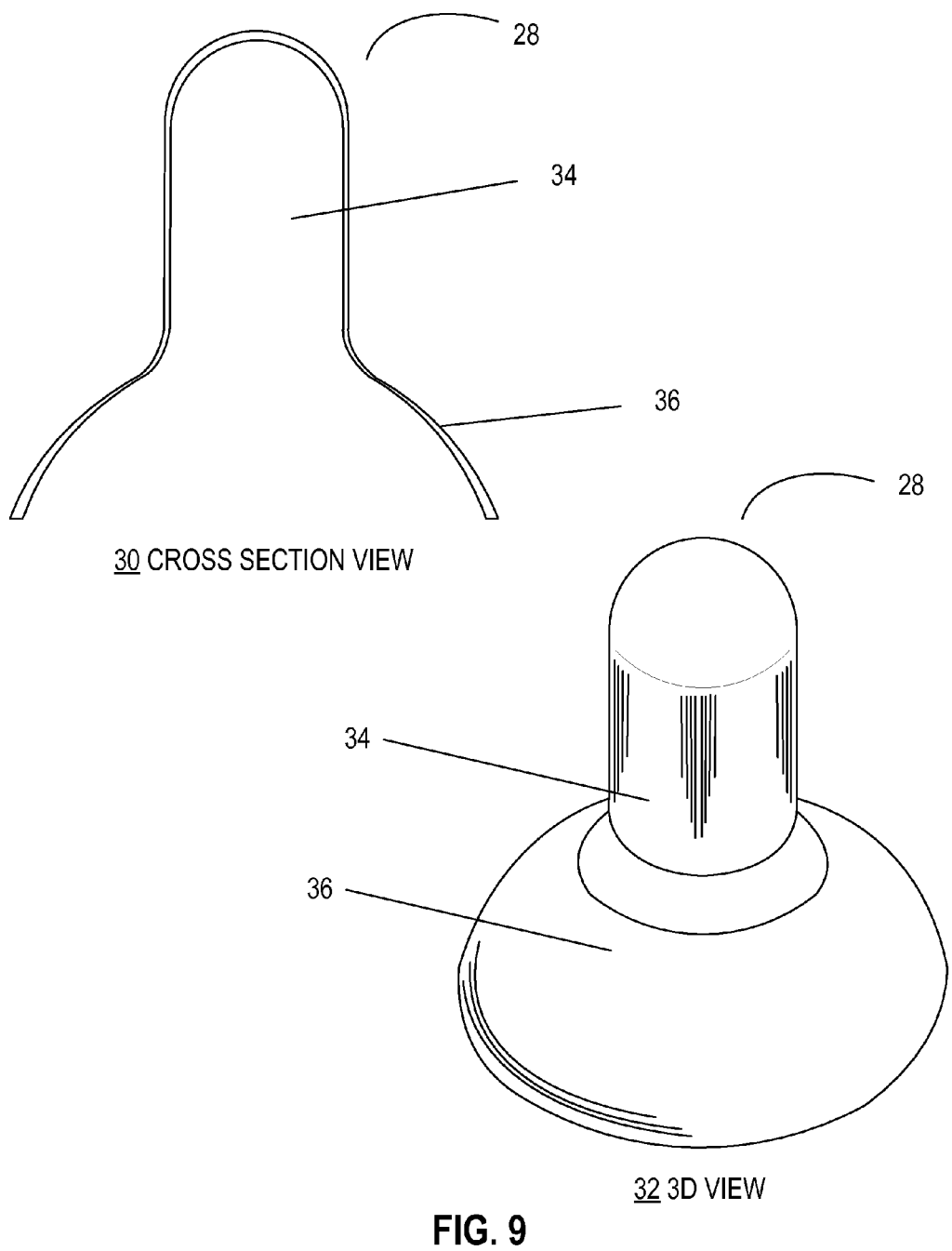
FIG. 9 is a diagram showing several views of a reservoir cap, according to some embodiments of the invention.

FIG. 9 illustrates views of reservoir cap 28 according to some embodiments of the invention. View 30 illustrates a cross-sectional view of reservoir cap 28, and view 32 illustrates a view reflecting the height, width, and depth of reservoir cap 28. Reservoir cap 28 comprises reservoir 34 for containing ejaculate. Reservoir cap 28 further comprises flange 36 formed at the opening of reservoir 34. Flange 36 has a shape for maintaining contact with the contour of a penile glans when applied thereto. While reservoir cap 28 is shown with a particular shape or configuration, it is understood that reservoir cap 28 may be differently shaped without departing from the spirit of embodiments of the invention. According to embodiments of the invention, reservoir cap 28 comprises a flexible material such as silicone, polyurethane, latex rubber, or other flexible barrier material capable of preventing passage of undesired matter therethough, such as ejaculate and components therein, such as sperm and microorganisms.

Figure 10:
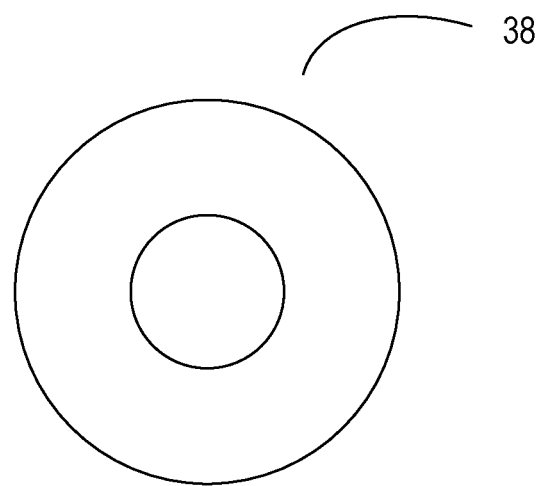
FIG. 10 is a diagrammatic view of an adhesive ring for application on the underside of the reservoir flange, according to some embodiments of the invention.

FIG. 10 illustrates an example of an adhesive ring 38 for applying to the underside of flange 36. In some embodiments, the adhesive ring is composed of a material, such as film or tape, with a double-sided pressure-sensitive adhesive coating, such as model number 1510 produced by the 3M Company. Such an adhesive ring is applied to the underside of the flange 36. In some other embodiments, the adhesive ring is an area of pressure-sensitive adhesive applied coating directly to the underside of the flange, which may be protected by a removable backing layer. While shown as a circular ring, it is understood that the adhesive ring 38 may be of a different shape for adhering to the underside of flange 36 without departing from the spirit of the invention.

Figure 11:
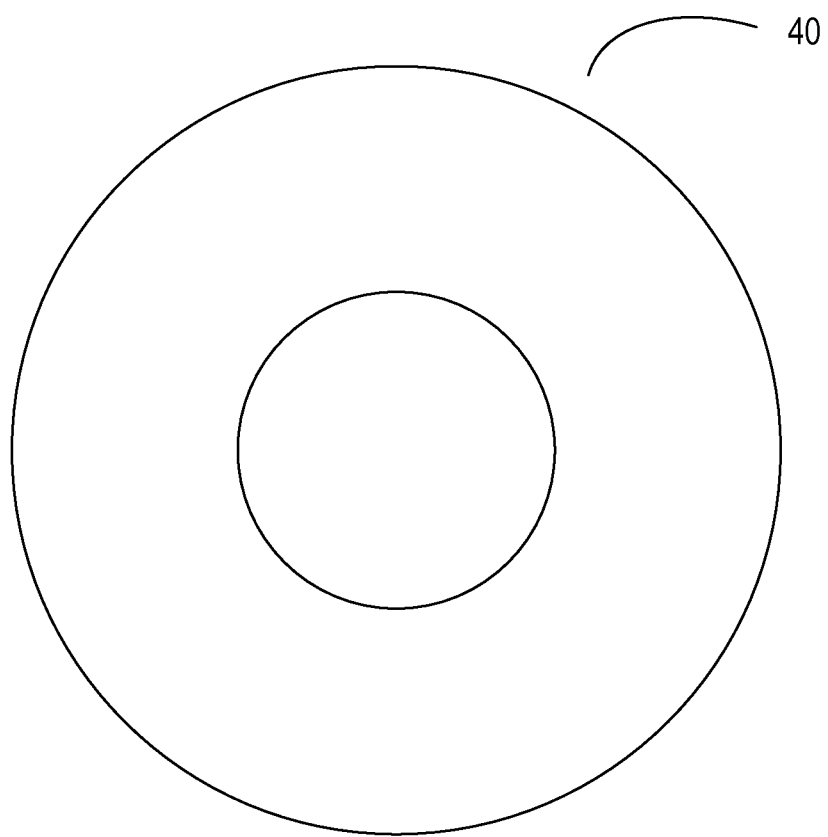
FIG. 11 is a diagrammatic view of a security ring for application over at least the reservoir flange and the base, according to some embodiments of the invention.

FIG. 11 illustrates an example of a security ring 40 for applying over reservoir flange 36, first base portion 10 and second base portion 22 for further creating a seal for avoiding leaking of fluid at the junction between reservoir cap 28 and base portions 10 and 22, and at the junction between base portions 10 and 22 and the skin. Application of security ring 40 also avoids detachment of reservoir cap 28 from the penis. A view of security ring 40 as applied is further shown and described with reference to FIG. 13. In some embodiments, security ring 40 is a ring-shaped patch composed of a material, such as film or tape, with side single-sided pressure-sensitive adhesive coating, such as the example material described above with reference to FIG. 1. While shown as a circular ring, it is understood that the security ring 40 may be of a different shape without departing from the spirit of the invention.

Figure 12:
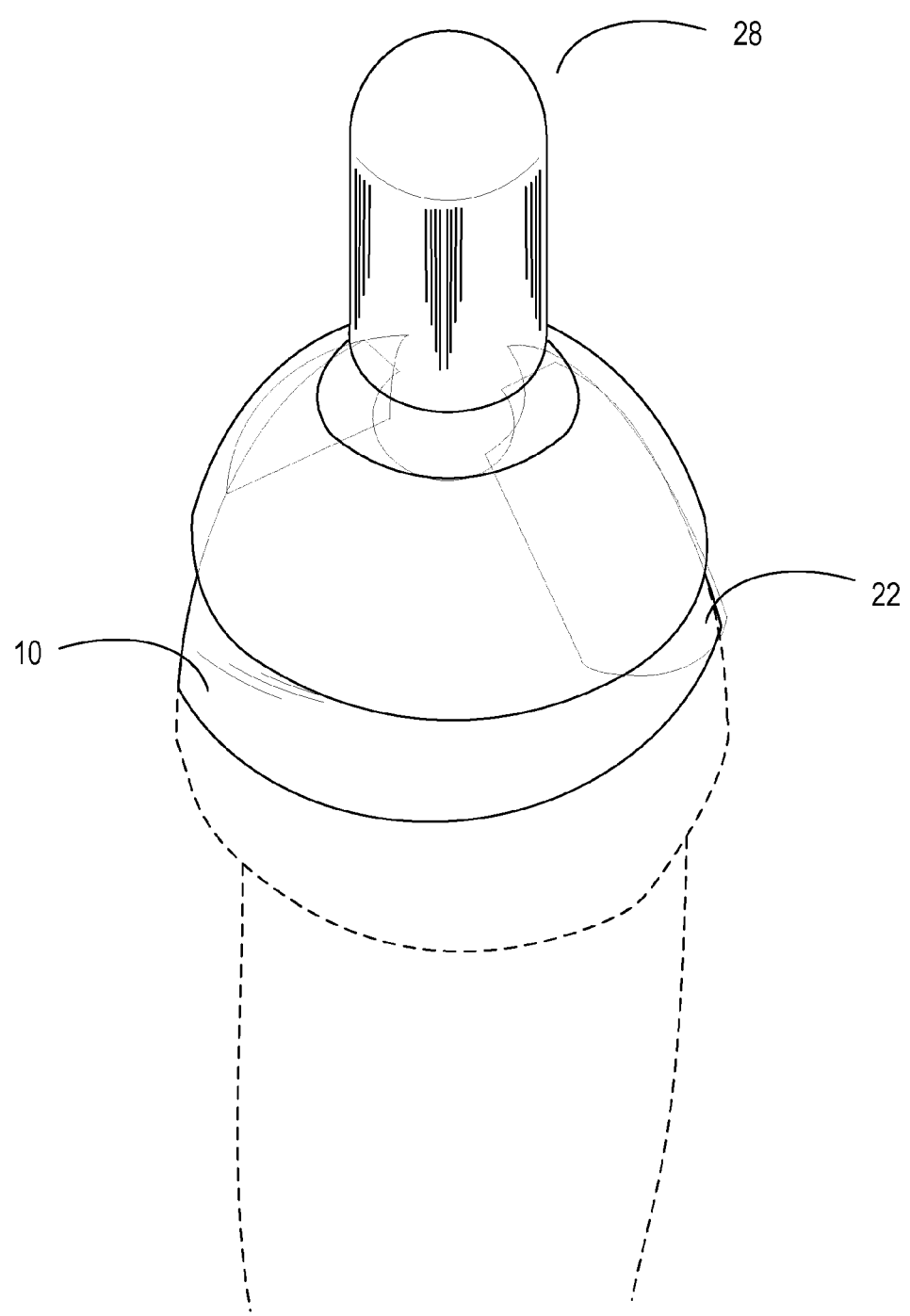
FIG. 12 is diagrammatic view of the relative approximate positions of a first and a second portion of the barrier device to form a base, and a reservoir cap when in use, according to some embodiments of the invention.

FIG. 12 illustrates an example view of reservoir cap 28 applied over first base portion 10 and second base portion 22 onto the penile glans. Reservoir cap 28 is adhered to base portions 10 and 22 by adhesive ring 38 (not shown) on the underside of flange 36. In some embodiments, the top surface of base portions 10 and 22 may also be coated with pressure-sensitive adhesive coating for better bonding. In some embodiments, the configuration shown in FIG. 12 is a completed application of the prophylactic device without the use of security ring 40. In a preferred embodiment, when the bond strength of adhesive ring 38 is sufficient for forming a leak-proof seal during coitus, security ring 40 is not used.

Figure 13:
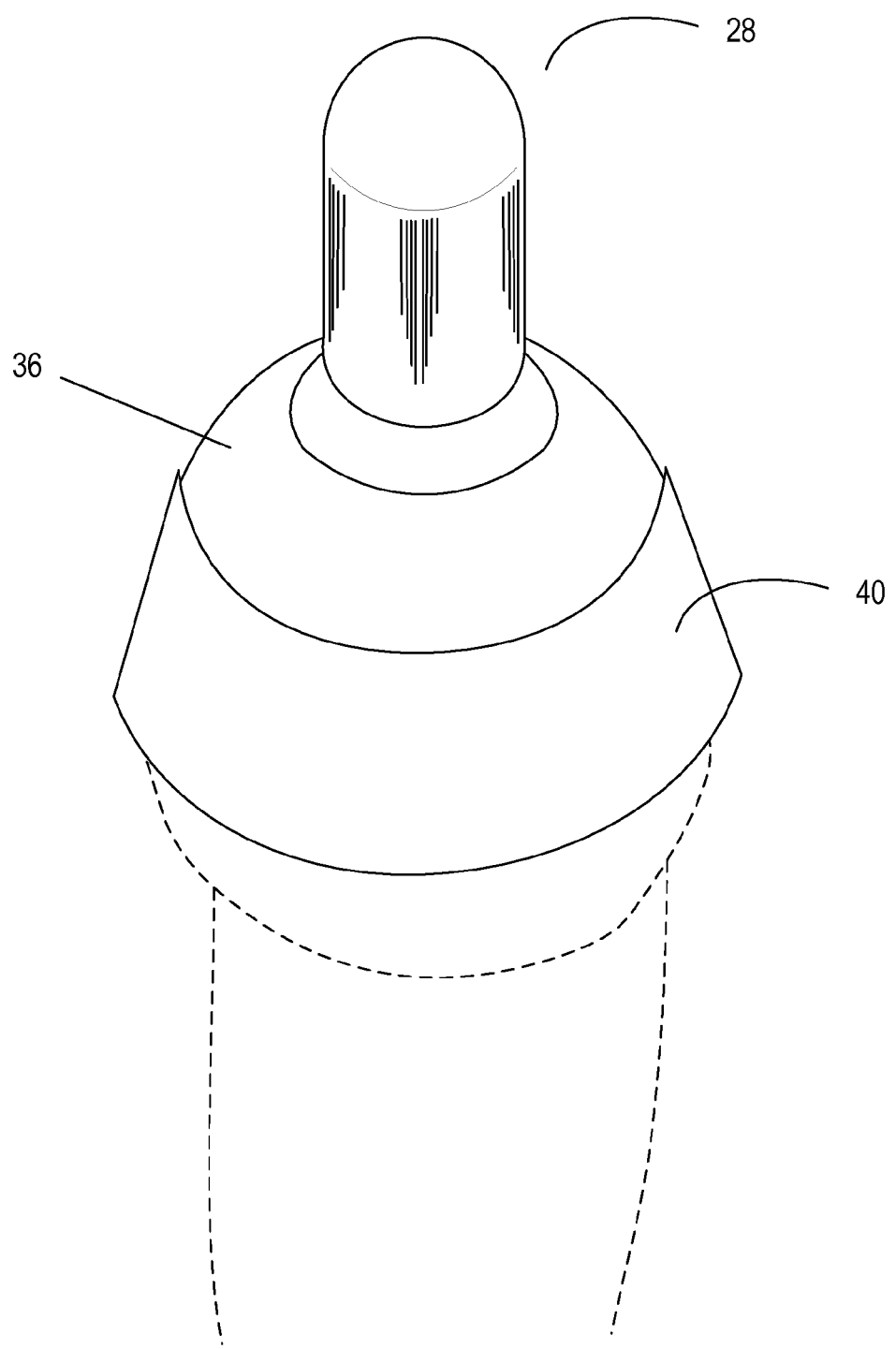
FIG. 13 is diagrammatic view of the relative approximate positions of a first and a second portion of the barrier device to form a base, a reservoir cap, and the security ring when in use, according to some embodiments of the invention.

FIG. 13 illustrates an example view of security ring 40 applied over flange 36 of reservoir cap 28. Security ring 40 covers at least a portion of flange 36 and a portion of base portions 10 and 22. As shown, security ring 40 as applied overlaps and covers the entire bottom edges of base portions 10 and 22.

Figure 14:
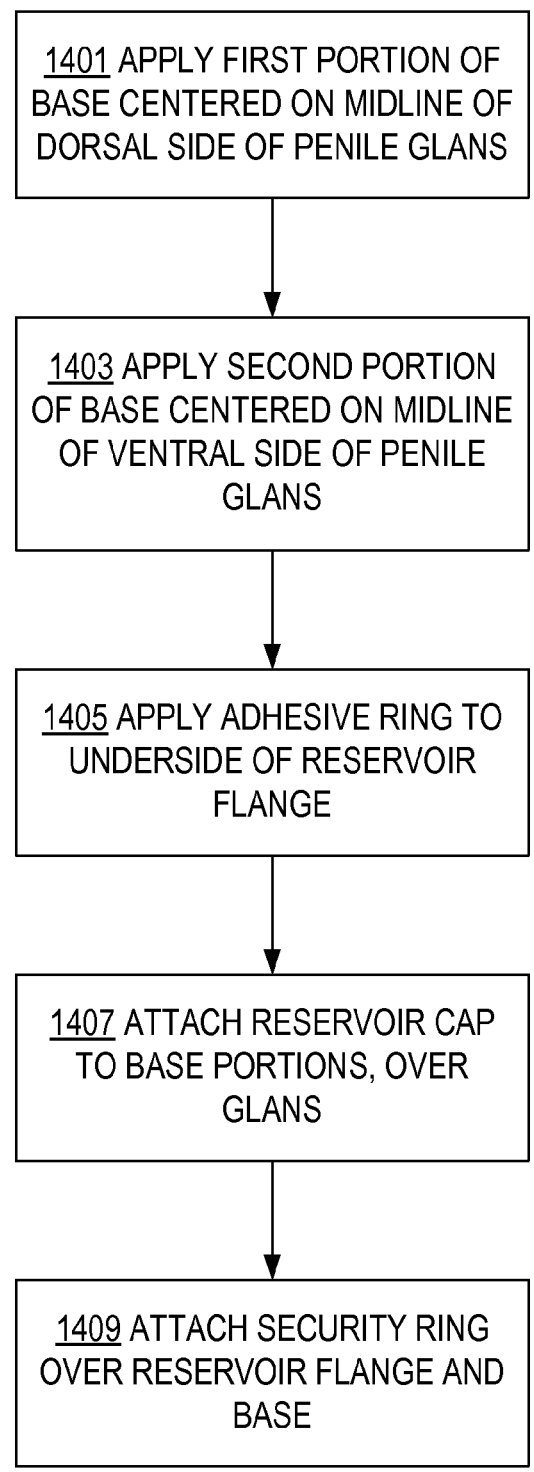
FIG. 14 is flow diagram illustrating an example process for using the device as shown in FIGS. 1-13, according to some embodiments of the invention.

FIG. 14 is a flow chart illustrating steps in the application of first base portion 10, second base portion 20, reservoir cap 28, adhesive ring 38, and security ring 40 according to embodiments of the invention. At step 1401, first base portion 10 is applied on the glans approximately centered on the midline of the dorsal side of the penile glans. First base portion 10 makes contact and bonds against the surface contour of the glans. In some embodiments, first base portion 10 has removable backing on one or more surfaces, which are removed in the process of executing step 1401. If first base portion 10 has a carrier backing for maintaining a stiffer structure for ease of handling, the carrier backing is removed after first base portion 10 is bonded onto the penile glans.

At step 1403, second base portion 22 is applied on the glans, approximately centered on the midline of ventral side of the penile glans. As with first base portion 10, if second base portion 22 has any removable backing, it is removed in the process of executing step 1403.

At step 1405, adhesive ring 38 is applied to the underside of flange 36 of reservoir cap 28. In some embodiments, adhesive ring 38 is a pressure-sensitive adhesive coating that is directly applied to the underside of flange 36 during the manufacturing process for reservoir cap 28.

At step 1407, reservoir cap 28 is applied to the base portions 10 and 22, over the glans. In some embodiments, a removable protective backing covers the exposed adhesive side of adhesive ring 38, which is removed before step 1407.

At step 1409, security ring 40 is applied over the junction boundary of the bottom edge of flange 36 and the base portions 10 and 22. In some embodiments, where the bond strength of adhesive 38 is sufficient to form and maintain a leak-proof seal during coitus, an additional security ring 40 is not used, and step 1409 is not performed.

Figure 15:
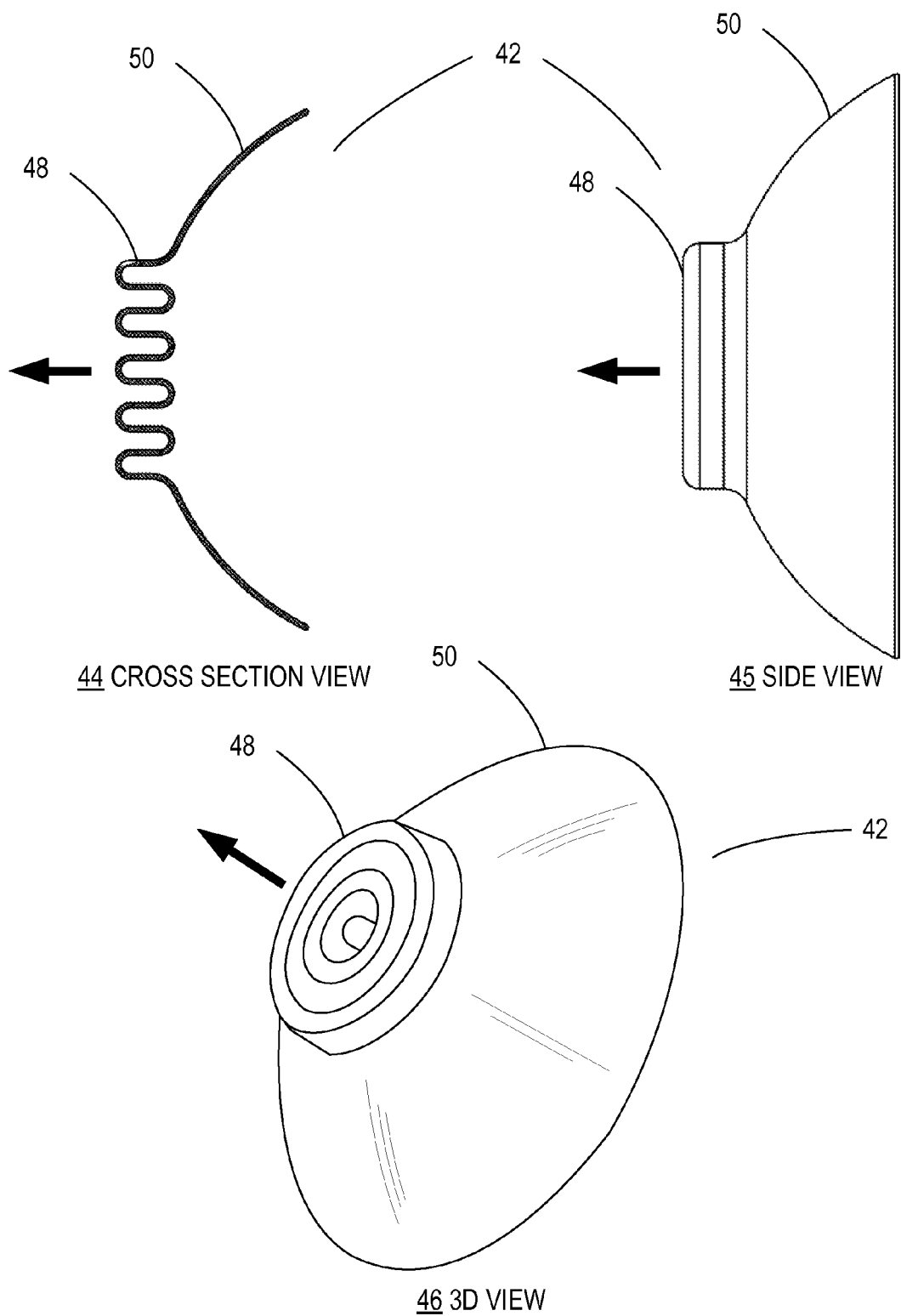
FIG. 15 is a diagram showing several views of an expandable reservoir cap, according to some embodiments of the invention.

FIG. 15 illustrates views of expandable reservoir cap 42 according to some embodiments of the invention. View 44 illustrates a cross-sectional view of reservoir cap 42, view 45 illustrates a side view of reservoir cap 42, and view 46 illustrates a view reflecting the height, width, and depth of reservoir cap 42, in the collapsed position. Reservoir cap 42 comprises expandable and collapsed reservoir 48 for containing ejaculate, which is collapsed as shown. Collapsed reservoir 48 includes concentric ridges, which when deformed in the direction indicated, provides a volume for receiving ejaculate. Reservoir cap 42 further comprises flange 50 formed at the outer boundary of expandable reservoir 48. Flange 50 has a shape for maintaining contact with the contour of a penile glans when applied thereto. While expandable reservoir cap 42 is shown with a particular shape and configuration, it is understood that expandable reservoir cap 48 may be differently shaped without departing from the spirit of embodiments of the invention. According to embodiments of the invention, reservoir cap 42 comprises a flexible material such as silicone, polyurethane, latex rubber, or other flexible barrier material capable of preventing passage of undesired matter therethrough, such as ejaculate and components therein, such as sperm and microorganisms. Reservoir cap 42 may be used with other components in the examples described above in place of reservoir cap 28.

Other features, aspects and objects of the invention can be obtained from a review of the figures and the claims. It is to be understood that other embodiments of the invention can be developed and fall within the spirit and scope of the invention and claims.

The foregoing description of preferred embodiments of the present invention has been provided for the purposes of illustration and description. It is not intended to be exhaustive or to limit the invention to the precise forms disclosed. Various additions, deletions and modifications are contemplated as being within its scope. The scope of the invention is, therefore, indicated by the appended claims rather than the foregoing description. Further, all changes which may fall within the meaning and range of equivalency of the claims and elements and features thereof are to be embraced within their scope.

What is claimed is:

1. A prophylactic device comprising:
  a base substrate comprising at least a first flexible structure for adhering the base substrate to a glans of a penis;
  a reservoir cap structure having a reservoir portion, said reservoir cap structure also having a flange portion for adhering against the base substrate, the flange portion for bonding with the base substrate to form a seal at a junction between the flange portion and the base substrate; and
  a security flexible structure with an aperture for receiving at least the reservoir portion, the security flexible structure having one adhesive coating for adhering the security flexible structure to at least the flange portion of the reservoir cap and the base substrate.

2. The prophylactic device of claim 1, the reservoir cap having an extendable reservoir.

3. The prophylactic device of claim 1, the base substrate further comprising a second flexible structure, the second flexible structure having at least one adhesive coating for adhering the second flexible structure to the glans of the penis, wherein the first flexible structure is configured for application centered along the dorsal side of the glans, and wherein the second flexible structure is configured for application centered along the ventral side of the glans.

4. The prophylactic device of claim 1, wherein the base substrate comprises a polyurethane film.

5. The prophylactic device of claim 1, wherein the base substrate comprises medical-grade adhesive film.

6. The prophylactic device of claim 1, the first flexible structure having an adhesive coating for adhering to a glans of a penis.

7. The prophylactic device of claim 1, the flange portion having an underside surface having an adhesive structure of any one of a material with double-sided adhesive coating, or an adhesive coating bonded to the underside surface.

8. The prophylactic device of claim 1, the base substrate configured to provide an opening over a penile meatus when the base substrate is bonded to the penile glans.

9. A method for sealing a reservoir from leakage of ejaculate, comprising the steps of:
   adhering to a glans of a penis a base substrate, the base substrate comprising at least a first flexible structure having at least one adhesive coating for said adhering;
   adhering against the base substrate a reservoir cap structure, the reservoir cap structure having a reservoir portion, said reservoir cap structure also having a flange portion for said adhering against the base substrate, the flange portion for bonding with the base substrate to form a seal at a junction between the flange portion and the base substrate; and
   adhering to at least the flange portion of the reservoir cap and the base substrate, a security flexible structure with an aperture for receiving at least the reservoir portion, the security flexible structure having one adhesive coating for said adhering.

10. The method of claim 9, the base substrate further comprising a second flexible structure, the second flexible structure having at least one adhesive coating for adhering to the glans of the penis,
   wherein the first flexible structure is configured for application centered along the dorsal side of the glans, and wherein the second flexible structure is configured for application centered along the ventral side of the glans.

11. The method of claim 9, wherein the base substrate comprises a polyurethane film.

12. The method of claim 9, wherein the base substrate comprises medical-grade adhesive film.

13. The method of claim 9, the flange portion having an underside surface having an adhesive structure of any one of a material with double-sided adhesive coating, or a adhesive coating bonded to the underside surface.

14. The method of claim 9, the base substrate configured to provide an opening over a penile meatus when the base substrate is bonded to the penile glans.

\* \* \* \* \*